United States Patent [19]

Zeidler et al.

[11] Patent Number: 4,888,437
[45] Date of Patent: Dec. 19, 1989

[54] ALKYL HYDROXYALKYL PHOSPHORIC ACID ESTERS

[75] Inventors: Ulrich Zeidler, Duesseldorf; Alfred Meffert, Monheim, both of Fed. Rep. of Germany

[73] Assignee: Henkel Kommanditgesellschaft auf Aktien, Duesseldorf, Fed. Rep. of Germany

[21] Appl. No.: 69,788

[22] Filed: Jul. 2, 1987

[30] Foreign Application Priority Data

Jul. 4, 1986 [DE] Fed. Rep. of Germany ....... 3622440

[51] Int. Cl.$^4$ .............................................. C07F 9/09
[52] U.S. Cl. ................................................... 558/105
[58] Field of Search ............... 558/114, 115, 105, 177

[56] References Cited

U.S. PATENT DOCUMENTS

| 4,258,448 | 3/1981 | Reitz et al. | 558/105 X |
| 4,350,645 | 9/1982 | Kurosaki et al. | 558/114 X |
| 4,382,042 | 5/1983 | Hardy et al. | 558/115 |
| 4,736,051 | 4/1988 | Wakatsuki et al. | 558/105 |

FOREIGN PATENT DOCUMENTS 1812849 6/1970 Fed. Rep. of Germany .
2517985 6/1983 France .

OTHER PUBLICATIONS

Chemical Abstract, 70:57128X.

Primary Examiner—Ferris H. Lander
Attorney, Agent, or Firm—Ernest G. Szoke; Wayne C. Jaeschke; Real J. Grandmaison

[57] ABSTRACT

Alkyl hydroxyalkyl orthophosphoric acid esters, particularly mixtures thereof, corresponding to the following formula

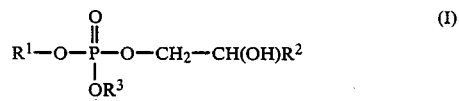

in which $R^1$ and $R^2$ represent $C_6$–$C_{22}$ alkyl groups and $R^3$ is hydrogen, a group $R^1$ or a group —$CH_2$—CH(OH)—$R^2$. The esters are prepared by reaction of phosphorus pentoxide with fatty alcohol and reaction of the phosphoric acid partial esters formed with long-chain α-epoxides. After conversion of the compounds corresponding to formula I, in which $R^3$ is hydrogen, into the salt form, the new alkyl hydroxyalkyl orthophosphoric acid ester mixtures are particularly suitable as emulsifiers for oil-water emulsion.

18 Claims, No Drawings

ALKYL HYDROXYALKYL PHOSPHORIC ACID ESTERS

BACKGROUND OF THE INVENTION

1. Field of the Invention:

This invention relates to new alkyl hydroxyalkyl orthophosphoric acid esters, mixtures thereof, and to a process for their production. The invention also relates to the use of the esters, particularly salts of the ester mixtures, as emulsifiers in cosmetic emulsions.

2. Description of Related Art:

The production of o-phosphoric acid partial esters by reaction of fatty alcohols with phosphorus pentoxide and the use of these esters and water-soluble salts thereof as surfactants and more especially as cosmetic emulsifiers has been known for some time. It is also known that phosphoric acid can be reacted with long-chain α-epoxides to form phosphoric acid-2-hydroxyalkyl esters, for example in accordance with U.S. Pat. No. 3,487,130.

Although the use of esters such as the above, more especially the water-soluble salts of the partial esters, as emulsifiers for cosmetic and other emulsions has long been known, it has now surprisingly been found that finer and more stable emulsions can be produced with alkyl hydroxyalkyl phosphoric acid esters and their mixtures.

DESCRIPTION OF THE INVENTION

Other than in the operating examples, or where otherwise indicated, all numbers expressing quantities of ingredients or reaction conditions used herein are to be understood as modified in all instances by the term "about".

Accordingly, the present invention relates to new alkyl hydroxyalkyl orthophosphoric acid esters, corresponding to the following formula $$R^1-O-\overset{\overset{O}{\|}}{\underset{OR^3}{P}}-O-CH_2-CH(OH)R^2 \quad (I)$$

in which $R^1$ and $R^2$, which may be the same or different, are straight or branched chain $C_6$–$C_{22}$ alkyl groups and $R^3$ is hydrogen, a group $R^1$ or a group $-CH_2-CH(OH)-R^2$. Particularly good emulsifier properties are shown by alkyl hydroxyalkyl orthophosphoric acid ester mixtures corresponding to formula I and preferably those in which $R^1$ and $R^2$ are linear $C_{10}$–$C_{18}$ alkyl groups.

The new alkyl hydroxyalkyl orthophosphoric acid esters, particularly mixtures, may be produced by a very simple process. This process, to which the invention also relates, is characterized in that 1 mole phosphorus pentoxide is reacted with 3 moles of a primary fatty alcohol of the formula $R^1$—OH or with 3-x moles of the fatty alcohol and x moles water, where x has a value of from 0 to 1. The orthophosphoric acid partial ester mixture formed is then reacted with from 0.5 to 3 moles and preferably with from 0.5 to 2 moles of an epoxide of the formula

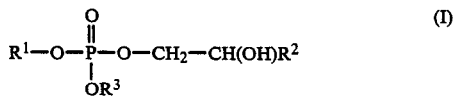

In these formulae, $R^1$ and $R^2$ have the same meaning as defined earlier above for formula I. The reaction of the phosphorus pentoxide with fatty alcohol takes place in accordance with the following scheme:

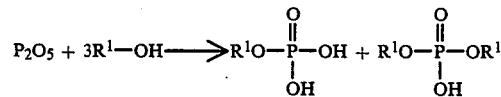

to form a mixture of phosphoric acid monoesters and diesters of the fatty alcohol. If less than 3 moles fatty alcohol are used per mole $P_2O_5$, fatty alcohol esters of pyrophosphoric acid or of polyphosphoric acids are formed, depending on the molar ratio used. In this case, water has to be added for cleavage of the P—O—P—bonds still present. However, at least 2 moles fatty alcohol should be used per mole $P_2O_5$ if the ester mixtures according to the invention are to be obtained as the main product. The mixture of orthophosphoric acid monoesters and diesters of the fatty alcohol obtained in this way is then reacted with from 0.5 l to 3 moles of an α-epoxide, preferably a linear 1-epoxy alkane corresponding to the formula

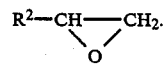

In this reaction, the α-epoxide is partly oligomerized so that the ester mixture also contains as secondary products phosphoric acid esters in which the group —CH$_2$—CH(OH)R$^2$ is replaced by a group —(CH$_2$—CHR$^2$O)$_m$H, where m represents the degree of oligomerization of the epoxide. In this way, only some of the P—OH—groups remain intact, even where 3 moles of the epoxide are used (per mole $P_2O_5$), which is reflected in the acid number of the phosphoric acid ester mixture.

Preferably, 1 mole phosphorus pentoxide is reacted with 3 moles of a linear primary fatty alcohol and the phosphoric acid partial ester mixture formed is reacted with 0.5 to 2 moles of the epoxide.

The reaction of the $P_2O_5$ with the fatty alcohol is exothermic and the reaction temperature should be maintained with cooling in a range of from 70° to 100° C. The reaction of the phosphoric acid-fatty alcohol partial ester with the α-epoxide is also exothermic and should be cooled to maintain the reaction temperature in a range of from 70° to 120° C. which will result in light-colored reaction products.

The alkyl hydroxyalkyl orthophosphoric acid ester mixtures according to the invention are characterized by a more or less high acid number (about 70-175), depending on their content of compounds corresponding to formula I in which $R^3$ is hydrogen. After neutralization with bases, such as alkali hydroxide or amines, they are suitable for use as surface-active agents and more especially as emulsifiers for technical and cosmetic purposes. The hydroxyl number of the mixture of esters will generally be in the range of 40 to 90. They are particularly suitable for the conversion of cosmetic oils and fats into stable, finely divided oil-in-water emulsions. Cosmetic oil and fat components of the type in question are, for example natural oils of the unsaturated triglyceride oil type, such as for example olive oil, sunflower oil or almond oil; hydrocarbon oils, such as for example paraffin oil; liquid fatty acid esters, such as for example, hexyl laurate, decyl oleate, isooctyl stearate, isopropyl myristate, oleyl oleate; synthetic triglycerides, such as for example caprylic and capric acid triglyceride; fatty alcohols, such as for example oleyl alcohol; synthetic branched alcohols, such for example 2-octyl dodecanol, 2-hexyl decanol, isostearyl alcohol and many other natural and synthetic oils and fats known as cosmetic oil and fat components.

Accordingly, the invention also relates to oil-in-water emulsions comprising (a) water, (b) an oil component and (c) an alkyl hydroxyalkyl orthophosphoric acid ester corresponding to formula I noted earlier, which will generally be employed as the salt of the mixture of esters produced according to the process described earlier. The alkyl hydroxyalkyl orthophosphoric acid ester mixtures according to the invention are preferably used in conjunction with other known emulsifiers and consistency regulators, rather than on their own. Known components in conjunction with which the alkyl hydroxyalkyl orthophosphoric acid ester mixtures may be used are, for example, fatty acid partial glycerides, i.e. mixtures of glycerol monoesters and diesters of $C_{16}$-$C_{22}$ fatty acids and cetyl-stearyl alcohol mixtures. For the use of the alkyl hydroxyalkyl orthophosphoric acid ester mixtures as emulsifiers, the compounds of formula I in which $R^3$ is hydrogen have to be converted into the alkali metal salt, such as sodium or potassium, ammonium salts, or the salts of other aliphatic or alicyclic, primary, secondary or tertiary amines or alkanolamines containing from 1 to 12 C-atoms, for example into the mono-, di- or trialkanolammonium salts containing from 2 to 4 C-atoms in the alkanol group, into the mono-, di- or trialkylammonium salts containing from 1 to 4 C-atoms in the alkyl group or into the morpholinium salts. This may be done, for example, by forming the salts by addition of the bases in a stoichiometric quantity, based on the acid number of the alkyl hydroxyalkyl phosphoric ester mixtures, and using the salts thus formed as emulsifiers. However, the acidic alkyl hydroxyalkyl phosphoric acid ester mixtures may also be added to the oil phase and the base to the aqueous phase of the emulsion, so that the salts acting as emulsifier are only formed during emulsification.

The alkyl hydroxyalkyl phosphoric acid esters according to the invention are best used in quantities of from 0.1 to 10% by weight, based on the emulsion as a whole. They are preferably used in quantities of from 0.5 to 5% by weight together with from 1 to 25% by weight (based on the emulsion) of standard coemulsifiers, such as fatty acid partial glycerides or cetyl-stearyl alcohol.

The oil-in-water emulsions obtainable in this way are stable, finely divided and particularly smooth and lustrous and are therefore particularly attractive in appearance. Accordingly, they are eminently suitable for use as cosmetic skin-care preparations.

The invention is illustrated by the following Examples.

EXAMPLES

1. Production Examples

General procedure

Three moles of a $C_{12}$-$C_{14}$ fatty alcohol mixture (hydroxyl number 290) were placed in a reaction vessel at 20° C., followed by the gradual addition with stirring of 1 mole phosphorus pentoxide. After the reaction temperature had risen to 80° C. under the effect of the heat of reaction, this temperature was maintained by cooling during the further addition of $P_2O_5$ and then for another 2 hours. By this time, an esterification product semi-solid at 20° C. and consisting of a mixture of phosphoric acid monoesters and diesters of the fatty alcohol had formed, its acid number being 225.

A linear $\alpha$-epoxyalkane in an amount of n moles as shown in the Table below was added dropwise at 50° C. to this esterification product. Another exothermic reaction began. The temperature was kept by cooling at 90° C. On completion of the addition, the mixture was stirred for 2 hours at 90° C. By this time, the content of epoxide oxygen in the reaction mixture had fallen to 0.

Wax-like to solid, colorless to pale yellow products having the characteristics shown in the following Table were obtained.

TABLE

| Example | 1.1 | 1.2 | 1.3 | 1.4 | 1.5 | 1.6 |
|---|---|---|---|---|---|---|
| $R^1OH$ | lauryl-myristyl (70:30 weight ratio) alcohol mixture, OH No.: 290 | | | | | |
| $R^2$—CH—CH$_2$ \\ O / | 1-epoxydodecane/ 1-epoxytetradecane (50:50 weight ratio) mixture, epoxide oxygen: 7.65% by weight | | | 1-epoxyhexadecane/ 1-epoxyoctadecane (50:50 ratio) mixture, epoxide oxygen: 5.41% by weight | | |
| n (moles epoxide per mole $P_2O_5$) | 1 | 0.6 | 1.4 | 1 | 0.6 | 1.4 |
| Acid number | 106.2 | 150.0 | 76.1 | 109.4 | 153.0 | 73.1 |
| Hydroxyl number | 69.4 | 56.7 | 83.3 | 48.0 | 50.9 | 53.6 |
| % by weight P | 6.2 | 7.0 | 5.5 | 5.62 | 6.5 | 4.8 |

2. Testing of the Emulsifying Effect:

The emulsifiers according to 1.1 to 1.6 were converted into the N,N-dimethyl ethanolammonium salts by addition of N,N-dimethyl ethanolamine (DMEA) in a quantity corresponding to the acid number. The DMEA salts obtained in this way were introduced as emulsifiers into the test emulsions according to Table II. The emulsions were prepared in the usual way by combining the emulsifiers and fatty components at a temperature around 70° C., adding the aqueous phase heated to 75° C. with vigorous stirring and cooling to 20° C. after formation of the emulsion. The emulsions were stored for 50 days at $-6°$ C., $+23°$ C. and $+40°$ C. Thereafter, there was no discernible change in the fineness or stability of the emulsions.

The composition of the emulsions was as shown in Table II:

TABLE II

| Example | 2.1 | 2.2 | 2.3 | 2.4 | 2.5 | 2.6 |
|---|---|---|---|---|---|---|
| DMEA salt of Example 1.1 to 1.6 | 3 | 0.7 | 3 | 1.5 | 1.5 | 4 |
| Cutina MD | 16 | 16 | — | 16 | 16 | 16 |
| Lanette 0 | — | — | 10 | — | — | — |
| Paraffin oil, thickly liquid | 6 | 6 | 5 | — | 6 | — |
| Eutanol G | — | — | 5 | — | — | 20 |
| Cetiol V | 6 | 6 | — | 10 | 6 | — |
| Almond oil | — | — | — | — | — | 15 |
| Myritol 318 | 6 | 6.8 | — | 10 | 6.5 | — |
| Propylene glycol | — | — | — | — | — | 5 |
| Glycerol | — | — | 5 | — | — | — |

TABLE II-continued

| Example | 2.1 | 2.2 | 2.3 | 2.4 | 2.5 | 2.6 |
|---|---|---|---|---|---|---|
| Water | 63 | 64.5 | 77 | 57.5 | 64 | 40 |

The trade name products used in the compositions listed in Table II are as follows:

Cutina TM MD: a mixture of mono- and diglycerides of palmitic and stearic acid (CTFA name: glyceryl stearate)

Lanette TM O: cetyl-stearyl alcohol (CFTA name: cetearyl alcohol)

Eutanol TM G: 2-octyl dodecanol

Cetiol TM V: oleic acid decyl ester (CTFA name: decyl oleate)

Myritol TM 318: caprylic/capric acid triglyceride (CFTA name: caprylic/capric triglyceride)

All these products are commercial products made by Henkel KGaA, 4000 Duesseldorf (Federal Republic of Germany).

We claim:

1. An alkyl hydroxyalkyl orthophosphoric acid ester having the formula

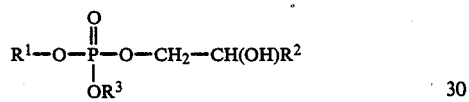

in which $R^1$ and $R^2$ is an alkyl group having from 6 to 22 carbon atoms and $R^3$ is hydrogen, $R^1$ or $-CH_2-CH(OH)R^2$.

2. A mixture of alkyl hydroxyalkyl orthophosphoric acid esters having the formula

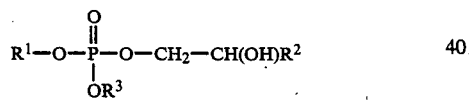

in which $R^1$ and $R^2$ are alkyl groups having from 6 to 22 carbon atoms and $R^3$ is selected from the group consisting of hydrogen, $R^1$ and $-CH_2-CH(OH)R^2$.

3. A salt of the mixture of esters defined in claim 2.

4. A salt as defined in claim 3 in which said salt is selected from the group consisting of an alkali metal, an amine salt, an ammonium salt and an alkanolamine salt in which the alkanol group contains from 1 to 12 carbon atoms.

5. A salt as defined in claim 4 in which said salt is the dimethyl ethanol ammonium salt.

6. A mixture of esters as defined in claim 2 wherein $R^1$ and $R^2$ are alkyl groups having from 10 to 18 carbon atoms and $R^3$ is hydrogen.

7. A mixture of esters as defined in claim 6 wherein $R^1$ and $R^2$ are different alkyl groups.

8. A mixture of esters as defined in claim 2 wherein $R^1$ and $R^2$ are alkyl groups having from 10 to 18 carbon atoms and $R^3$ is $-CH_2-CH(OH)R^2$.

9. A mixture of esters as defined in claim 8 in which $R^1$ and $R^2$ are different alkyl groups.

10. A mixture of esters as defined in claim 2 having an acid number in the range of about 70 to about 175.

11. A process for preparing alkyl hydroxyalkyl orthophosphoric acid esters comprising the steps of:

(a) reacting phosphorus pentoxide with a fatty alcohol of the formula $R^1OH$ in which $R^1$ is an alkyl group having from 6 to 22 carbon atoms to provide a mixture of phosphoric acid esters of said fatty alcohol, and (b) subsequently reacting said mixture of phosphoric acid esters of step (a) with an epoxide of the formula

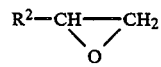

where $R^2$ is an alkyl group having 6 to 22 carbon atoms, thereby providing a mixture of alkyl hydroxyalkyl esters of the formula

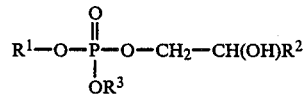

where $R^1$ and $R^2$ are as defined above and $R^3$ is selected from the group consisting of hydrogen, $R^1$ and $-CH_2-CH(OH)R^2$.

12. A process as defined in claim 11 in which at least 2 moles of said fatty alcohol are reacted with 1 mole of said phosphorus pentoxide and the resulting mixture of phosphoric acid esters from step (a) are reacted with 0.5 to 3 moles of said epoxide.

13. A process as defined in claim 12 in which from 0.5 to 2 moles of said epoxide are reacted with the mixture of phosphoric acid esters from step (a).

14. A process as defined in claim 12 in which 3 moles of said fatty alcohol is reacted with 1 mole of said phosphorus pentoxide.

15. A process as defined in claim 14 in which said fatty alcohol is a mixture of lauryl and myristyl alcohols.

16. A process as defined in claim 15 in which said epoxide is a mixture of 1-epoxydodecane and 1-epoxytetradecane.

17. A process as defined in claim 15 in which said epoxide is a mixture of 1-epoxyhexadecane and 1-epoxyoctadecane.

18. A process as defined in claim 11 in which the reaction in step (a) is conducted at a temperature in the range of from about 70° to about 100° C. and the reaction in step (b) is conducted at a temperature in the range of from about 70° to about 120° C.

* * * * *